United States Patent [19]

Muldary et al.

[11] 4,149,403
[45] Apr. 17, 1979

[54] DETERMINING STEAM QUALITY

[75] Inventors: Patrick F. Muldary, Walnut Creek; Erdal Tansev, San Francisco, both of Calif.

[73] Assignee: Chevron Research Company, San Francisco, Calif.

[21] Appl. No.: 804,219

[22] Filed: Jun. 7, 1977

[51] Int. Cl.² ............................................. G01N 7/00
[52] U.S. Cl. ...................................................... 73/29
[58] Field of Search .................. 73/29, 192, 211, 213; 138/44

[56] References Cited

U.S. PATENT DOCUMENTS

| 1,586,825 | 6/1926 | Meredith et al. | 138/44 |
| 1,698,318 | 1/1929 | Mapelsden | 73/213 X |
| 2,284,013 | 5/1942 | Pardoe | 73/213 |
| 2,501,593 | 3/1950 | Becker | 138/144 |
| 3,363,460 | 1/1968 | Baumann | 73/213 X |

Primary Examiner—Herbert Goldstein
Attorney, Agent, or Firm—R. L. Freeland, Jr.; George W. Wasson; Edward J. Keeling

[57] ABSTRACT

Method and apparatus for determining the quality of wet steam flowing in a steam line utilizing the relationship between critical flow pressure ($P_c$) and upstream pressure ($P_u$) to develop a critical pressure ratio $P_c/P_u$ to obtain the steam water mixture inlet enthalpy (H) from empirical curves and the steam quality from the equation:

$$\text{Steam Quality} = [(H-h_w)/(h_s-h_w)]P_u$$

where
$h_w$ = specific enthalphy of water, and
$h_s$ = specific enthalpy of steam bath both at $P_u$.

1 Claim, 4 Drawing Figures

PRESSURE PROFILES IN 6" CRITICAL FLOW CHOKES FOR A MEASURED UPSTREAM QUALITY OF 76.5%

4,149,403

DETERMINING STEAM QUALITY

FIELD OF THE INVENTION

The present invention relates to determining the approximate quality (i.e., the steam-to-water ratio by weight) of steam flowing in a steam line. More particularly, the present invention relates to a method and apparatus for determining steam quality of wet steam flowing in a steam line by establishing critical flow in the steam line and obtaining upstream pressure in the steam line ($P_u$) and critical pressure in the critical flow portion of the steam line ($P_c$) to provide a critical pressure ratio $P_c/P_u$ and relating the critical pressure ratio to experimentally derived curves of $P_c/P_u$ versus steam water mixture inlet enthalpy to obtain a basis for calculating steam quality.

BACKGROUND OF THE INVENTION

During generation and use of steam, it is often desirable to know the quality of the steam. Various techniques have evolved for measuring steam quality. The more common of these techniques involve using various colorimeters and orifice meters. Other techniques are available utilizing properties of feed water compared to the properties of the liquid phase of the steam. A discussion of these techniques is given in U.S. Pat. No. 3,596,516, issued Aug. 3, 1971. There have also been proposals to determine steam quality using captured samples of the steam water mixture. None of the techniques of determining steam quality, however, has been entirely satisfactory for field use. There is, therefore, still need for a method and apparatus for readily determining the quality of steam flowing in a steam line.

Heretofore, William G. Steltz, in an article titled "The Critical and Two-Phase Flow of Steam" in the *Journal of Engineering Power* of April, 1961, related a critical pressure ratio of $P_{exhaust}/P_{inlet}$ to inlet enthalpy in computer studies. Steltz, however, made several assumptions which are not applicable to actual field determination of the quality of wet steam flowing in a steam line. Other articles of background interest related to two-phase flow include: "Critical Two-Phase, Steam-Water Flows," by H. Fauske, from *Proceedings of the 1961 Heat Transfer and Fluid Mechanics Institute;* "Steam-Water Critical Flow Through Pipes," by Russell James, from the *Institution of Mechanical Engineers,* Vol. 176, No. 26, 1962; "Some Improved Steam Property Calculation Procedures," by R. B. McClintock and G. J. Silvestri, from the *Journal of Engineering for Power,* April, 1970; "Metering of Steam-Water Two-Phase Flow by Sharp-Edged Orifices," by Russell James, from the *Institution of Mechanical Engineers,* Vol. 180, Pt. 1, No. 23, 1965–66.

BRIEF DESCRIPTION OF THE INVENTION

The present invention relates to a method of determining the quality of wet steam flowing through a flow line from a steam generator to a downline location. Critical flow is established in an elongated choke bore located in a portion of the flow line between the steam generator and the downline location. The pressure in the flow line upstream of the critical flow portion ($P_u$) is measured and the pressure in the critical flow portion of the choke bore ($P_c$) is also measured. From these two pressures, the critical pressure ratio $P_c/P_u$ is determined. Curves of critical pressure ratio versus steam water mixture enthalpy are experimentally established for the chokes being used. Then for any given flow conditions, the critical pressure ratio $P_c/P_u$ and the upstream pressure $P_u$ are read and the wet steam inlet enthalpy (H) in BTU/LBM is determined from the curves. Steam quality in the flow line is then determined utilizing an equation where steam quality equals $$[(H - h_w)/(h_s - h_w)]P_u$$

where
  $h_w$ = specific enthalpy of water in BTU/LBM, and
  $h_s$ = specific enthalpy of steam in BTU/LBM both at $P_u$.

The present invention also includes apparatus for determining the quality of wet steam flowing through a steam line from a steam generator to a downstream location. A steam line is extended from a steam generator to a downstream location. A choke having an elongated bore for producing critical flow of wet steam through at least a portion of the choke is connected in the steam line between the steam generator and the downstream location. First pressure sensing means for determining the pressure in the steam line are connected upstream of the choke and second pressure sensing means for determining the pressure in the critical flow portion of the choke are connected to the choke.

OBJECTS OF THE INVENTION

The principal object of the present invention is to determine steam quality based on the relationship between the critical pressure ratio $P_c/P_u$, the upstream pressure $P_u$ and steam-water mixture inlet enthalpy. Further objects and advantages of the present invention will become apparent from the following detailed description read in view of the accompanying drawings which are incorporated herein.

DETAILED DESCRIPTION OF PREFERRED EMBODIMENT

Figure 1:
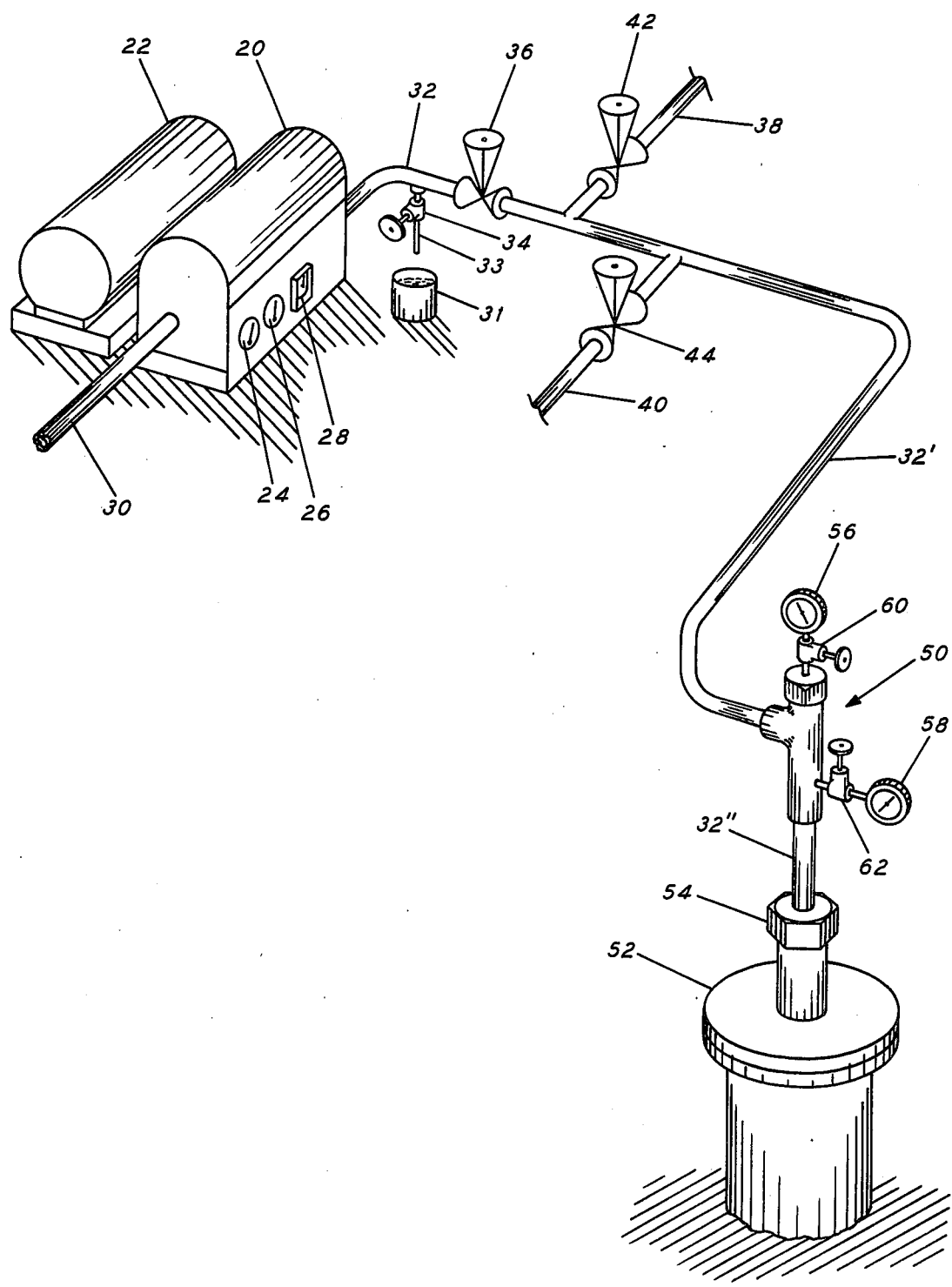
FIG. 1 is a schematic perspective view and illustrates apparatus assembled in accordance with the preferred embodiment of the present invention.

FIG. 1 is a schematic perspective view illustrating the preferred form of apparatus assembled in accordance with the present invention. A wet steam generator 20 is provided with a source of fuel such as tank 22. Water suitable for conversion to wet steam enters the generator through pipe 30. The water is converted to wet steam of a desired quality in the generator 20 and leaves the generator through steam line 32 as a mixture of water and steam. A valve 36 is located on steam line 32 to control flow down the line. Typically, the steam generator is provided with instruments including a flow rate gauge 24, a generator pressure gauge 26 and a flow recorder 28. A means for obtaining a downstream generator water sample is provided and includes a valve 34 tapped into steam line 32. A suitable stub end 33 and receptical 31 are used to collect a sample. As known in the art, the quality of the steam leaving the generator 20 can be determined using data obtained from the instruments and sample.

In typical oilfield operations utilizing wet steam a plurality of steam lines are fed from the same steam generator. Thus, steam line 38 having control valve 42 and steam line 40 having control valve 44 may branch off of steam line 32'. Because of flow splitting phenomena at these branches, different proportions of steam and water will most probably enter each steam line. It is, therefore, often necessary to measure steam quality at a given downstream location, such as for example, immediately upstream of the wellhead 52 of a steam injection well.

In accordance with the invention, a choke as illustrated generally by the number 50 is connected into the steam line 32', 32" at a predetermined downstream location between the steam generator 20 and the steam injection wellhead 52. The choke includes an elongated bore portion for producing critical flow of the wet steam through at least a portion of its length. The choke is provided with suitable piping 32" and connection 54 for delivering the output to the wellhead 52 of the steam injection well. A first pressure sensing means such as pressure gauge 56 is connected upstream of the critical flow portion of choke 50 for use in determining the pressure in the steam line 32' upstream of the critical flow-portion of the choke. A suitable valve 60 controls flow to the gauge 56. Thus, the valve 60 may be closed and the gauge 56 may be removed when pressure readings are not required. A second pressure sensing means such as pressure gauge 58 is connected into the choke 50 in the critical flow portion thereof for determining the critical flow pressure of the wet steam flowing through the choke $P_c$. The critical pressure $P_c$ and the upstream pressure $P_u$ provide a critical pressure ratio $P_c/P_u$ useful in determining steam quality in the steam line at the choke 50 location.

Figure 2:
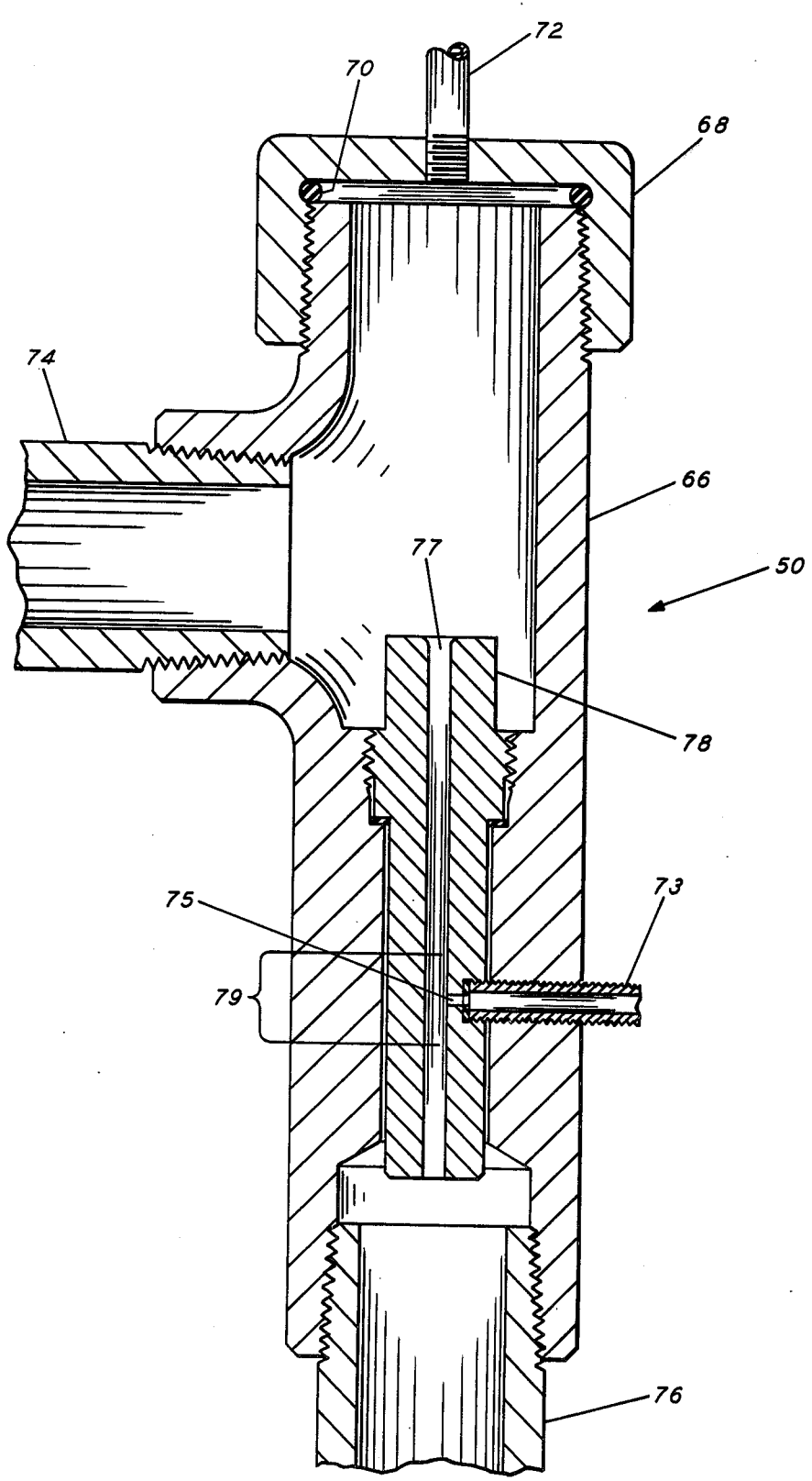
FIG. 2 is a section view and illustrates a choke including an elongated bore portion useful in producing critical flow of wet steam therethrough.

FIG. 2 is a sectional view of the choke 50. With reference then to both FIGS. 1 and 2, a choke body 66 has suitable threads for connecting sub 74 which connects to upstream steam line 32' and for connecting sub 76 which connects to downstream steam line 32". The upper end of the choke body 66 is closed by a suitable cap 68 and O-ring 70. A pressure tap is provided with tube 72 which extends through valve 60 to pressure gauge 56 to provide for determining the pressure upstream of the critical flow portion of the choke. The choke includes an elongated bore such as a restricted flow beam 78 having a reduced diameter bore 77 connected inside the choke body 66. The wet steam flows through the elongated bore 77 and critical flow of the wet steam occurs in at least a portion (indicated by numeral 79) of the bore 77 of the choke 50. A tap 75 for a pressure gauge tube 73 is located in the critical flow portion of the choke and extends to pressure gauge 58 through valve 62. Thus, the pressure can be determined in the critical flow portion of the choke. Elongated bore chokes of constant diameter are used in the present invention. The elongated bore must be of sufficient length so that critical flow will occur and critical pressure can be measured. The present invention will generally be most applicable in constant bore chokes of at least 2" in length. The particular length of the bore is, of course, dependent on the operating pressure and flow rate of a given system.

Figure 3:
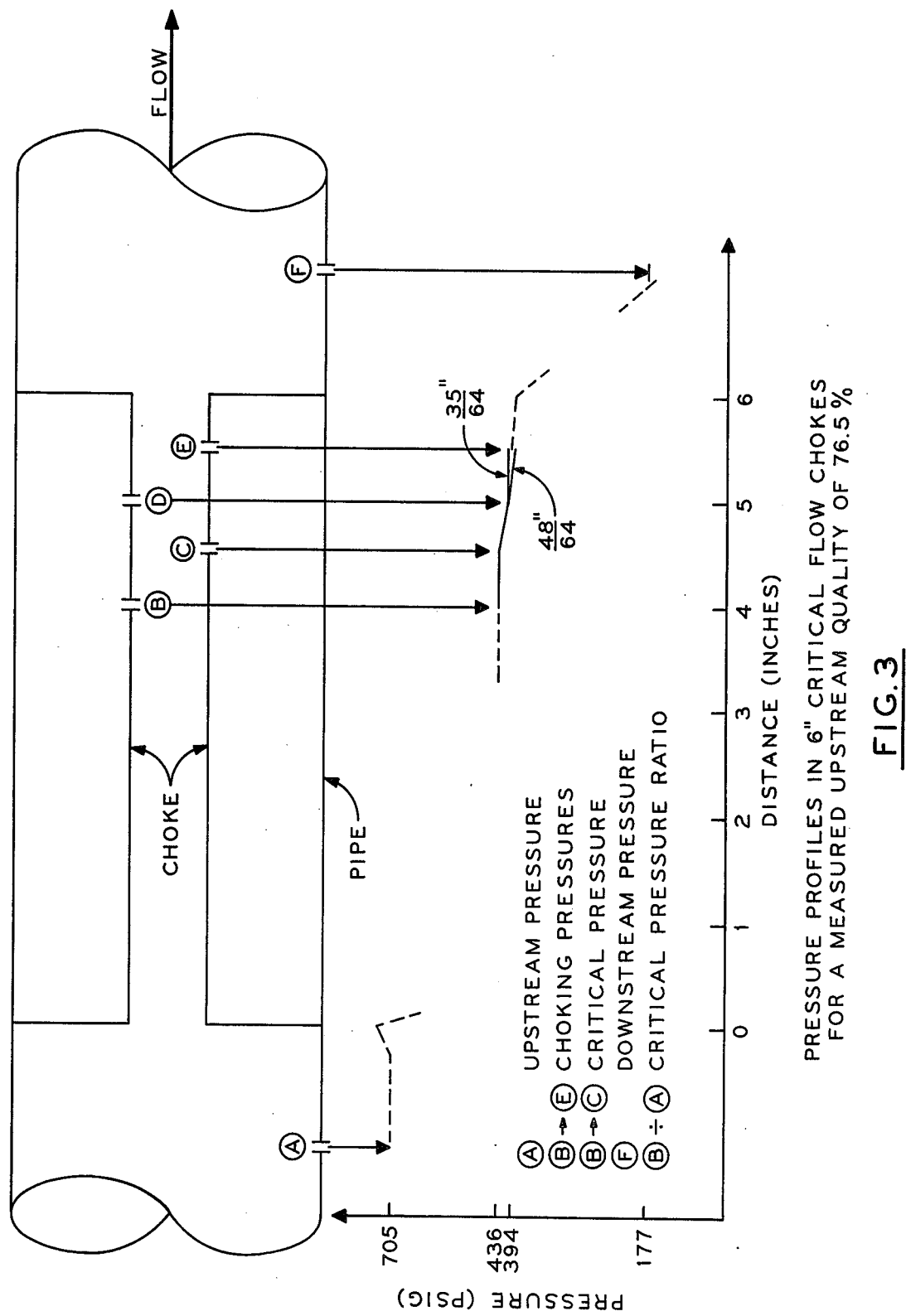
FIG. 3 is a chart showing pressure profiles in critical flow chokes.

FIG. 3 is a chart showing pressure profile curves in 6" critical flow chokes for a measured upstream quality of 76.5%. The curves are for both 48/64" and 35/64", six-inch long choke bores. The pressure in the choke was taken at a number of locations (B–E). A constant pressure reading (B–C) was obtained and this pressure is the critical pressure. A tap (A) was also provided for obtaining upstream pressure. Data was collected during a series of runs using a choke set up as illustrated in FIG. 3 and from the data the experimental critical flow curves for steam water mixtures shown in FIG. 4 were obtained. Steam quality then for given pressure readings is determined using the relationships described herein and these curves.

Figure 4:
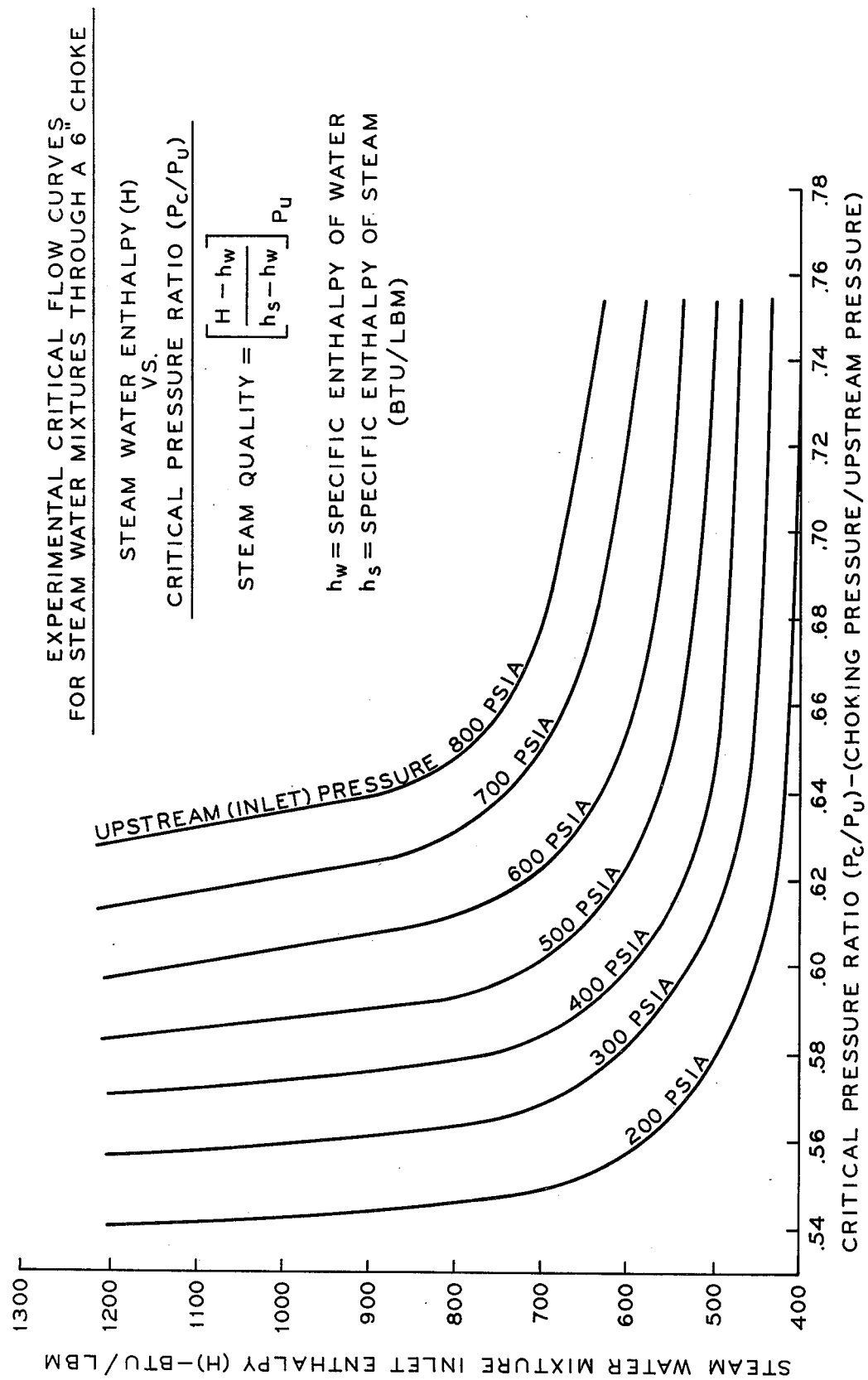
FIG. 4 is a graph illustrating experimental critical flow curves for wet steam mixtures through a choke.

The curves illustrated in FIG. 4 are experimental critical flow curves for steam water mixtures through a six-inch choke. Two different choke bores were used in developing these curves. Thus, both a 35/64" bore and a 48/64" bore were used in the runs. The curves of FIG. 4 are believed to be applicable to any standard, conventional bore for common six-inch oil field chokes. Experimental critical flow curves can be developed for steam water mixture critical flow through any choke. A series of $P_c$ and $P_u$ readings are then taken and the $P_c/P_u$ ratio is determined. The steam quality for each set of readings is determined by conventional methods for the mixture leaving the choke. For example, the steam water mixture leaving the choke is directed to a conventional separator where the steam phase is measured through an orifice meter installed in a line coming from the top of the separator and the water phase is meausured through an orifice meter installed in a line coming from the bottom of the separator. The ratio of the flows will give steam quality. The steam quality is converted to steam water inlet mixture enthalpy by calculation. Points are plotted to get the experimental curves for various conditions. These curves may then be used in accordance with the present invention.

Thus, a method is provided for determining the quality of wet steam flowing through a steam line from a stream generator to a downline location. Critical flow is established in a portion of the steam line between the steam generator and the downline location. The pressure in the steam line upstream of the critical flow portion ($P_u$) is measured. The pressure in the critical flow portion of the steam line ($P_c$) is also measured. The critical pressure ratio $P_c/P_u$ is determined. Then based on the critical pressure ratio $P_c/P_u$ and experimental curves analogous to FIG. 4, the wet steam inlet enthalpy (H) in BTU/LBM is found and finally steam quality in the steam line is found utilizing an equation where steam quality equals $$[H-h_w/h_s-h_w]P_u$$

where
$h_w$ = specific enthalpy of water in BTU/LBM, and
$h_s$ = specific enthalpy of steam in BTU/LBM both at $P_u$.

Although certain preferred embodiments of the present invention have been described in detail herein, the invention is not limited to only these embodiments, but rather by the scope of the appended claims.

What is claimed is:

1. A method of determining the quality of wet steam comprising flowing wet steam through a flow line from a steam generator to a downline location, establishing critical flow in a portion of an elongated constant diameter choke located in said flow line between said steam generator and said downline location, determining the location in said choke of said critical flow portion, measuring the pressure in said flow line upstream of said critical flow portion ($P_u$), measuring the critical pressure in said critical flow portion of said choke ($P_c$), determining the critical pressure ratio $P_c/P_u$, establishing experimental critical flow curves at various pressures for steam water mixtures in critical flow in said critical flow portion of said choke, determining the wet steam inlet mixture enthalpy (H) in BTU/LBM from said experimental critical flow curves for steam water mixtures in critical flow in said critical flow portion and determining steam quality in said flow line utilizing an equation where steam quality equals $$[H - h_w/h_s - h_w]P_u$$

where
 $h_w$ = specific enthalpy of water in BTU/LBM, and
 $h_s$ = specific enthalpy of steam in BTU/LBM both at $P_u$.

* * * * *